(12) United States Patent
Zschernack et al.

(10) Patent No.: US 7,823,444 B2
(45) Date of Patent: Nov. 2, 2010

(54) DEVICE AND PROCESS FOR MEASURING THE VELOCITY OF FLOW OF A FLUID USING PULSE SIGNAL GENERATED BASED ON FEEDBACK

(75) Inventors: Ulf Zschernack, Bad Schwartau (DE); Henning Gerder, Lübeck (DE); Hartmut Stark, Stockelsdorf (DE)

(73) Assignee: Dräger Medical AG & Co. KG, Lübeck (DE)

( * ) Notice: Subject to any disclaimer, the term of this patent is extended or adjusted under 35 U.S.C. 154(b) by 113 days.

(21) Appl. No.: 12/241,610

(22) Filed: Sep. 30, 2008

(65) Prior Publication Data
US 2009/0133490 A1 May 28, 2009

(30) Foreign Application Priority Data
Nov. 27, 2007 (DE) .................. 10 2007 057 027

(51) Int. Cl.
*G01F 1/68* (2006.01)
(52) U.S. Cl. .................. 73/204.26; 73/204.15
(58) Field of Classification Search ............ None
See application file for complete search history.

(56) References Cited

U.S. PATENT DOCUMENTS

| 4,787,251 | A | * | 11/1988 | Kolodjski .............. 73/755 |
| 5,339,687 | A | | 8/1994 | Gimson et al. |
| 5,522,261 | A | * | 6/1996 | Grover et al. ............ 73/204.18 |
| 5,719,341 | A | * | 2/1998 | Reynolds et al. ......... 73/861.95 |
| 5,783,805 | A | * | 7/1998 | Katzmann ................. 219/494 |
| 5,918,268 | A | * | 6/1999 | Lukas et al. ............. 73/40.5 R |
| 6,234,016 | B1 | * | 5/2001 | Bonne et al. ............ 73/204.26 |
| 6,518,847 | B1 | * | 2/2003 | Sauer ......................... 331/66 |

FOREIGN PATENT DOCUMENTS

| DE | 19647350 A1 | 5/1998 |
| DE | 102005000964 B3 | 7/2006 |
| WO | WO 01/18500 A1 | 3/2001 |

* cited by examiner

*Primary Examiner*—Harshad Patel
(74) *Attorney, Agent, or Firm*—McGlew and Tuttle, P.C.

(57) ABSTRACT

A device is provided for measuring the velocity of flow of a fluid in a respiration system and includes a first thermal sensor element (5) provided with a controllable heating element (50) and a second thermal sensor element (6). The thermal sensor elements (5, 6) are arranged at spaced locations from one another at a path of flow, so that a thermal signal generated by the first sensor element (5) with the heating element (50) is transmitted to the second sensor element (6), and the second sensor element (6) is designed to detect the thermal signal from the fluid flow. The second sensor element (6) is connected to the first sensor element (5) via feedback (12) which triggers another thermal signal. A controlling and analyzing device (13, 15) is connected to the sensor elements (5, 6) to start the generation of a first thermal signal and to read and analyze the signal frequency as an indicator of the velocity of flow.

25 Claims, 7 Drawing Sheets

DEVICE AND PROCESS FOR MEASURING THE VELOCITY OF FLOW OF A FLUID USING PULSE SIGNAL GENERATED BASED ON FEEDBACK

CROSS REFERENCE TO RELATED APPLICATIONS

This application claims the benefit of priority under 35 U.S.C. §119 of German Patent Application DE 10 2007 057 027.0 filed Nov. 27, 2007, the entire contents of which are incorporated herein by reference.

FIELD OF THE INVENTION

The present invention pertains to a device and a process for measuring the velocity of flow of a fluid, i.e., of a gas or of a liquid-gas mixture, in a respiration system.

BACKGROUND OF THE INVENTION

Accurate measurement of the volume flow of the breathing gas, e.g., within the flexible breathing tube, is of particular interest in respiration systems. The velocity of flow of the fluid is the relevant variable to be measured here for the determination of the volume flow of a fluid through a known conduit cross section.

Hot-wire or hot-film anemometers are used in many cases to measure the velocity of flow of a gas used for respiration. These are associated with the advantage that they do not represent any appreciable flow resistance themselves. A hot-wire or hot-film anemometer comprises a thin heated element, the so-called hot wire or hot film, which is cooled by the fluid flowing past it. The resistance of the wire or film is measured, which itself depends on the temperature. Depending on the value of the velocity of flow of the fluid flowing past, the hot wire or hot film is cooled more or less intensely, so that the resistance is an indicator of the velocity of flow of the fluid flowing past.

Another advantage of these elements is the small thermal mass of the measuring element itself. The measurement is extensively independent of the temperature when the temperature of the hot wire or hot film is more than 250° C. above the fluid temperature, and fluid temperature measurement and compensation can now be eliminated. For applications with overtemperatures of less than 150° C., an additional "cold wire" is needed to compensate changes in the gas temperature. The "hot wire" and the "cold wire" are connected to this end in a Wheatstone bridge, and the hot wire is adjusted to a constant overtemperature relative to the cold wire, so that the heating current being fed depends directly on the amount of heat removed per unit of time with the fluid flow. This conventional operation of the hot-wire or hot-film anemometer is called constant-temperature anemometer mode (CTA mode).

However, besides the volume flow of the fluid flowing past, the absolute temperature of the fluid relative to the hot wire or hot film as well as the composition of the fluid and hence the thermal conductivity and heat capacity of the fluid also affect the extent of cooling, so that these parameters must be taken into account, in principle, when measuring the velocity of flow, if they are subject to relevant changes.

A device and a process for measuring a volume flow difference between the inspiratory volume flow and the expiratory volume flow by means of temperature anemometry are known from DE 10 2005 000 964 B3.

DE 196 47 350 A1 discloses a device and a process for measuring the volume flow of gases. The run time of a thermal signal between two measuring means along the direction of flow of the gas is determined here.

It is described in WO 01/18500 A1 (corresponding to U.S. Pat. No. 5,339,687) how a mass flow measurement is obtained with a heating element and two temperature sensors from the temperature signals of the temperature sensors taking into account measured, substance-specific characteristics to characterize the heat transmission characteristic.

It is especially important in respiration technique to measure the changes in the velocity of flow of the breathing gases accurately and especially rapidly. The problem was found in this connection that, for example, hot-film sensors based on planar semiconductor chips have relatively slow response times and above all slow fall times due to the storage of the amount of heat during rapid changes in the velocity of flow. While this problem can still be partially eliminated by a rapid adjustment and by a rapid rise of the heating current in case of a sudden rise in the velocity of flow (e.g., from 0 L/minute to 100 L/minute) in the CTA mode, the fall time will be 10 times higher than the rise time in case of an abrupt drop in the velocity of flow (e.g., from 100 L/minute to 0 L/minute). This is due to the fact that the regulator can only switch off the element but it cannot cool it. Switching off the heating for the element is not, moreover, meaningful, because there must be a potential difference on the bridge amplifier for a restart of the bridge circuit.

For example, sensor chips for measuring the velocity of flow of a fluid, in which two resistive heating elements and two resistive gas temperature elements are united on one membrane, are known from the Fraunhofer-Institut für Siliziumtechnologie (Fraunhofer Institute of Silicon Technology) in Itzehoe (ISIT). A heating element and a precision resistor each are connected in a gas temperature-compensating Wheatstone bridge in the CTA mode. The two bridges operate electrically fully autarchically. However, the heat transfer from one heating element to the other heating element is used as information due to the use of two heating elements, similarly to the device disclosed in DE 196 47 350 A1, because, due to the heat transfer, less heating current is needed in the heating element located downstream to maintain an overtemperature predetermined in the CTA mode. It is thus possible to recognize the direction of flow as long as the heat transfer does not drift at high velocities of flow of the fluid. The bridge located downstream is thus used as a direction indicator for the fluid flow, while the bridge that is located upstream and is in the CTA mode determines the amount of the velocity of flow. As an alternative, it is also possible to use the amount of the heat transfer from the heating element located upstream to the heating element located downstream as a difference of the heating current values needed as a measured value of the velocity of flow. However, the losses due to heat transfer which are caused by drifting are problematic at high velocities of flow.

However, the problem of the flow fall times is not solved by any of the prior-art devices nor by any of the prior-art processes. Furthermore, it is a fundamental problem of the hot-wire and hot-film anemometers that the characteristic describing the relationship between the velocity of flow and the heat transfer depends on the thermal conductivity properties of the fluid, i.e., on the thermal conductivity and heat capacity of the fluid, which are determined, among other things, by the composition, temperature and pressure of the fluid. The measurements must therefore be corrected by means of external information, e.g., concerning the fluid composition, in case of the prior-art devices and processes, or calibrated for certain fluids. Changes occurring in the fluid composition during the measurement cannot, in general, be

SUMMARY OF THE INVENTION

The object of the present invention is therefore to provide a device and a process for measuring the velocity of flow of a fluid, which overcome the drawbacks of the prior-art devices and processes, e.g., especially rapid fall times in case of abrupt drops in the velocity of flow. In addition, information on the fluid composition shall be able to be obtained during the measurement and used for the analysis of the velocity of flow.

According to a first aspect of the present invention, a device is provided for measuring the velocity of flow of a fluid in a respiration system. The device comprises a first sensor element and a second sensor element and a controlling and analyzing means. At least the first thermal sensor element is provided with a controllable heating element and the thermal sensor elements are arranged at spaced locations from one another at a flow path of the fluid in a respiration system, so that a thermal signal generated by the first sensor element with its heating element is transmitted during the flow of the fluid from the first sensor element to the second sensor element, and the second sensor element is designed to detect a transmitted thermal signal from the fluid. The second sensor element is connected to the first sensor element via feedback (a feedback signal via a feedback connection), so that each thermal signal generated by the first sensor element and detected by the second sensor element initiates the return of an electric feedback pulse signal to the first sensor element, which triggers the generation of another thermal signal by the heating element of the first sensor element. The controlling and analyzing means is connected to the thermal sensor elements and are set up in terms of circuitry and/or programming to start the operation by generating a first thermal signal by the first sensor element with a first pulse signal and to read and analyze, in the further course of the operation, the signal frequency of the feedback pulse signals, i.e., the frequency of feedback pulse signals per unit of time, as an indicator of the velocity of flow of the fluid.

According to a second aspect of the present invention, a process is provided for measuring the velocity of flow of a fluid in a respiration system by means of a first thermal sensor element and a second thermal sensor element. At least the first thermal sensor element is provided with a controllable heating element, wherein the sensor elements are arranged at spaced locations from one another at a flow path of the fluid in a respiration system, so that a thermal signal generated by the first sensor element is transmitted by a flow of the fluid from the first sensor element to the second sensor element, and wherein the second sensor element detects a first thermal signal, which is generated by the first sensor element and is transmitted by fluid flow. Furthermore, the generation of a first thermal signal by the first sensor element is started by a first pulse signal triggered by the controlling and analyzing means. Each thermal signal generated by the first sensor element and by the second sensor element now brings about the return of a feedback pulse signal to the first sensor element. The feedback pulse signal triggers the generation of another thermal signal by the first sensor element, and the signal frequency of the feedback pulse signals is read and analyzed as an indicator of the velocity of flow of the fluid during the further operation.

At least the first "thermal sensor element" is provided with a heating element for generating a selected amount of heat and is a sensor element, which is suitable for a hot-wire or hot-film anemometer and whose heating capacity can be detected. The second sensor element may, in principle, also be suitable exclusively for detecting a thermal signal and not for generating one. However, the second thermal sensor element is preferably also provided, corresponding to the first one, with a controllable heating element, and the first thermal sensor element and the second thermal sensor element can now be especially components of an identical design.

The term "thermal signal" means here a signal of limited duration and of any shape, which is generated by heat transfer from the heating element into the fluid and can be detected by the other thermal sensor element and is suitable for transmitting a unit of information. This is preferably a locally elevated temperature of the fluid here, which is transmitted with the convection of the fluid flow from one sensor element to the other.

A "feedback pulse signal" can be amplified, shaped or modified as desired on its way between the sensor elements such that generation of a new thermal signal by the heating element of the first sensor element can thus be triggered. In particular, the feedback pulse signal can be sent to the input of a heating pulse generator, whereupon a voltage pulse is generated at the output of the heating pulse generator. This voltage pulse generates, furthermore, a thermal signal in the heating element of the first sensor element.

The "controlling and analyzing means" may comprise one or more units for signal processing and analysis, which are set up in terms of circuitry and programming to carry out the steps and functions intended as claimed. The controlling and analyzing means preferably comprise a converting unit for frequency measurement and an analyzing unit for determining the velocity of flow from the frequency measurement and optionally from other additional information.

The feedback of each thermal signal, which is generated by the sensor element located upstream and is detected by the sensor element located downstream, to the sensor element located upstream, which thereupon sends a new thermal signal to the fluid, causes a constant signal frequency of feedback pulse signals to be obtained in the feedback in case of a constant fluid flow between the sensor elements. A heating pulse generator is preferably connected in the device according to the present invention between the second sensor element and the first sensor element in order to transmit the feedback pulse signal in the form of an electrical heating pulse to the heating element of the first sensor element. To prevent an undesired resonant build-up from being generated during the feedback, the thermal signals are preferably pulses of a short pulse duration, while the first sensor element is switched "blind" for detecting feedback pulse signals from the feedback. Consequently, the highest measurable velocity of flow is limited by the pulse length of the thermal signals.

Measurement of the signal frequency is especially advantageous for determining the velocity of flow, because the analog signal of a heat transfer, which is known from the conventional CTA mode, is discretized in a certain way, and digital information, whose rise and fall times are equally fast, is available in the signal frequency of the feedback pulse signals. For example, no thermal signal is transmitted any longer from the first thermal sensor element to the second thermal sensor element when the fluid volume flow abruptly drops to zero, which interrupts the generation of feedback signals and thus immediately yields a display for a significant reduction of flow.

The distance between the sensor elements may be selected, for example, so small at one mm that the signal frequency is high enough, even at relatively low velocities of flow, to make it possible to determine the signal frequency and hence the velocity of flow more rapidly than in the conventional CTA mode, especially in case of sudden drops, for example, within the framework of an averaging. In addition, it becomes possible to use simple microcontrol elements for the controlling and analyzing means, because, contrary to operation in the CTA mode, no sensitive signal amplifier is needed for weak analog signals or an analog-digital converter.

In an exemplary arrangement in a cell with an inner cross-sectional area of 133 mm$^2$, in which the two sensor elements are arranged in the cell at a distance of 1 mm in the direction of the longitudinal axis of the cell, the maximum velocity of flow is fixed at 25 m/sec corresponding to a maximum volume flow of 200 L/minute through the cell. A run time of 40 μsec is thus obtained for the transmission of the thermal signal over a 1-mm section in the fluid, which corresponds to a frequency of 25 kHz. Since the pulse width may be ¼ to ½ of the run time as a maximum, pulses with a pulse length of at most 10 μsec would consequently have to be generated. A velocity of flow of 25 cm/sec and a signal frequency of 250 Hz would correspond here to a volume flow of 2 L/minute. A volume flow of 500 mL/minute would correspond to a velocity of flow of 62.5 mm/sec and to a signal frequency of 62.5 Hz. It will be clear to the person skilled in the art that the distance between the sensor elements or the cross-sectional area of the fluid conduit can be selected correspondingly in a suitable manner to obtain the optimal measurement for a certain volume flow measuring range.

If the velocity of flow is so low that determination of the signal frequency would take too long, for example, within the framework of an averaging over several signals, it is also possible to carry out a determination of the velocity of flow in the conventional CTA mode in an advantageous embodiment during a certain time, preferably during the signal pauses. The CTA mode during the pulse pauses can be operated, in principle, at all velocities of flow in order to have the largest possible amount of information available for the analysis of the velocity of flow. The measurement may also be switched over fully to the CTA mode automatically or manually above or below a certain velocity of flow.

The measured information from the operation in the CTA mode may be combined with the measured information from the pulsed operation as desired in the analyzing means in order to guarantee as error-free a determination of the velocity of flow as possible. For example, the information from the measurement in the pulsed operation can also be used to select a suitable, gas-specific characteristic describing the relationship between the velocity of flow and the heat transfer for the operation in the CTA mode.

The amplitude of the pulses can thus also be selected to be low and the signal frequency cannot be increased any more beginning from a certain upper limit, so that the pulses appear only as a waviness during the normal adjustment in the CTA mode beginning from a certain velocity of flow, and the heat transfer from one sensor element to the other is available as an integral over the pulses as information and can be stabilized at a constant level. This heat transfer obtained from the combination of CTA and pulsed operation can be used both for a measurement of the velocity of flow itself and for selecting gas-specific characteristics for the conventional CTA operation.

At least one of the sensor elements, but preferably both of them, are advantageously connected to a conventional constant-temperature anemometer circuit (CTA circuit) and they can thus also be analyzed in the conventional CTA mode. Such CTA circuits can be embodied by a Wheatstone bridge or another circuit, which makes possible the accurate measurement of the resistance or the heating capacity of the sensor element.

In a first advantageous embodiment of the device according to the present invention, the device additionally has at least one fluid temperature measuring element. Each sensor element preferably has a fluid temperature measuring element. The fluid temperature measuring element is arranged and designed to measure the fluid temperature in the environment of at least one sensor element. This fluid temperature measuring element corresponds to an above-mentioned "cold wire" for compensating changes in the gas temperature in order to also guarantee an accurate determination of the velocity of flow in the CTA mode at overtemperatures of only about 150° C. One sensor element and one fluid temperature measuring element each are preferably connected for this in the particular Wheatstone bridge, and each sensor element is stabilized at a constant overtemperature relative to the particular fluid temperature measuring element, so that the amount of heating power supplied depends directly on the amount of heat removed per unit of time with the fluid flow.

Not only the amount of the velocity of flow of the breathing gas, but also the direction of flow change over time in case of use in a flexible breathing tube. It is therefore also of interest to have the ability to determine both the direction of the flow and also the value of the velocity of flow in both directions of flow automatically, without manual intervention.

With another advantageous embodiment, the present invention offers a simple solution to this problem. The second sensor element is also designed here to send a thermal signal to the fluid. This thermal signal is transmitted by a flow of the fluid from the second sensor element to the first sensor element. The first sensor element is designed to receive a thermal signal from the fluid.

The device additionally has a switchover unit, which is designed to switch over the device alternatingly such that a thermal signal received by the second sensor element is returned to the second sensor element in the form of a feedback pulse signal for a certain time in order to trigger the generation of a new thermal signal by the second sensor element. The signal frequency of the feedback pulse signals can thus be read and analyzed as an indicator of the velocity of flow of the fluid in the direction from the second to the first sensor element. The sensor elements and the circuits connected thereto are advantageously of an identical design, so that a symmetrical arrangement is obtained, in which the switchover unit can change the roles played by the sensor elements as transmitters of thermal signals and as receivers of thermal signals between the two sensor elements. The switchover unit preferably switches over the device periodically when the actual velocity of flow drops below a lower limit of the velocity of flow until a velocity of flow above this lower limit in one direction or the other can be detected. Consequently, there is here a certain range around a velocity of flow of zero, in which no information can be obtained on the velocity of flow.

This drawback can be overcome in an alternative embodiment to the embodiment described above. However, a third sensor element, which is designed to detect a thermal signal from the fluid, is additionally needed in this alternative embodiment of the device. The third sensor element is arranged such that the first sensor element is located at the flow path of the fluid between the second and third sensor elements. It is connected to the first sensor element via a second feedback, so that a thermal signal detected by the third sensor element is returned in the form of a feed pulse signal to the first sensor element in order to trigger the generation of a new thermal signal by the first sensor element. Analogously to the preceding exemplary embodiments, the controlling and analyzing means is also connected to the second feedback and are designed to read and analyze the signal frequency of the feedback pulse signals in the two feedbacks as an indicator of the velocity of flow of the fluid in the direction from the first to the third sensor element. Consequently, the velocity of flow is measured here basically in parallel in both directions of flow, so that the difference of the two measured velocities of flow is available with a sign corresponding to the direction of flow. Since a thermal signal moves in this case almost exclusively by convection in the direction of the fluid flow, that measured value "against the flow" yields a signal frequency of zero and thus also zero velocity of flow in the direction opposite the flow. Consequently, the simultaneous measurement in both directions does not distort the velocity of flow with a sign, which was determined by the difference.

In another advantageous embodiment of the present invention, the amplitude of the pulse height can be varied or modulated. This can be embodied, for example, by the first sensor element not being adjusted to a constant overtemperature, but to a constant absolute temperature. The thermal conductivity properties of the fluid can be inferred by varying or modulating the amplitude of the thermal signals. Since the heat transfer from one sensor element to the other depends on the thermal conductivity and the heat capacity of the fluid at constant velocity of flow, the fluid can be characterized by these properties and a corresponding characteristic can be selected for the CTA operation. However, it is not only possible to select a corresponding characteristic for the CTA operation, but also to adjust effects by varying the fluid composition analogously to the gas temperature-compensating regulation within certain limits, so that potential errors caused by these variations can be compensated in the analysis of the velocity of flow.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
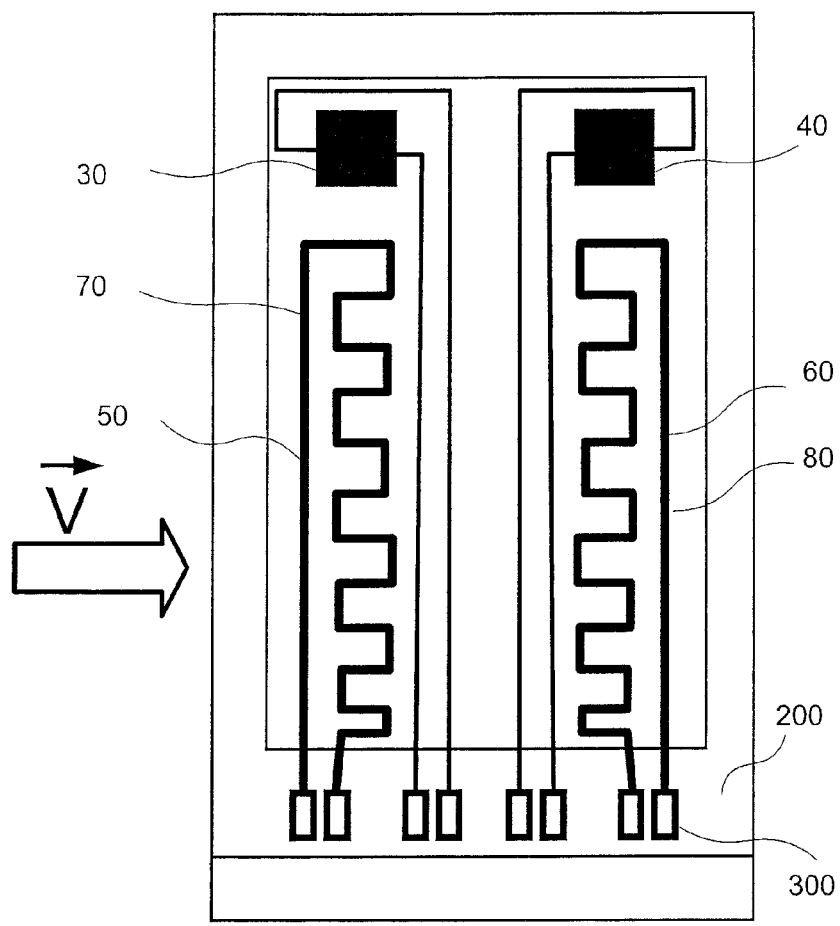
FIG. 1 is a schematic view showing the general layout of a sensor chip, as it is known from the state of the art.
Figure 2:
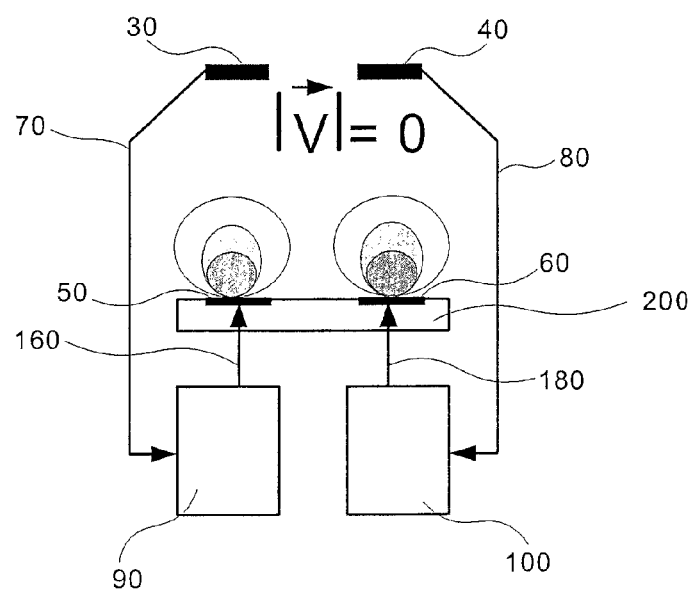
FIG. 2 is a schematic view showing the behavior of a sensor chip, as it is known from the state of the art, at zero velocity of flow.

Referring to the drawings in particular, the sensor chip 200 shown in FIG. 1 is known from the Fraunhofer-Institut für Siliziumtechnologie in Itzehoe (ISIT). Two resistive heating elements 50, 60 and two resistive gas temperature elements 30, 40 are united on one membrane in this sensor chip 200. One heating element 50, 60 each and one precision resistor 30, 40 are connected via the electric conductors 70, 80 as well as 160, 180 and the terminals 300 to a gas temperature-compensating Wheatstone bridge 90, 100 in the CTA mode, as is shown in FIG. 2. The two bridges 90, 100 operate electrically fully autarchically. However, the heat transfer from one heating element 50 to the other heating element 60 is used as information due to the use of the two heating elements 50, 60, because due to the heat transfer, less heating capacity is needed in the heating element 60 located downstream to maintain an overtemperature preset in the CTA mode. It thus becomes possible to recognize the direction of flow as long as the heat transfer does not drift at high velocities of flow of the fluid. The bridge 100 located downstream is thus used as a direction indicator for the fluid flow, while the bridge 90 located upstream determines the value of the velocity of flow in the CTA mode. As an alternative, it is also possible to use the value of the heat transfer from the heating element 50 located upstream to the heating element 60 located downstream as a difference of the needed heating currents as a measured value of the velocity of flow. However, losses due to heat transfer caused by drifting are problematic here at high velocities of flow.

FIG. 2 schematically shows the behavior of the thermal sensor chip 200 when the velocity of flow of the fluid equals zero. The two independent heating elements 50 and 60 are adjusted in the CTA mode to a certain overtemperature relative to the gas temperature measured in the gas temperature elements 30, 40 via the respective bridges 90, 100, which are connected to them via the electric conductors 160 and 180, respectively. Heat is released to the fluid at each heating element 50, 60, and this release of heat follows the temperature gradient, which is schematically indicated by "temperature level lines" within the fluid in the respective environments around the heating elements 50 and 60. The heating elements 50 and 60 are identical in this example, so that the release of heat to the fluid and hence also the electric heating currents of heating element 50 and of heating element 60, which currents are needed in the bridges 90 and 100, are also the same in both heating circuits if the velocity of flow of the fluid equals zero. This is also indicated by the symmetrical distribution of the temperature level lines. The particular heating current for the respective heating elements 50 and 60, which is needed in this situation, depends on the selected overtemperature in the CTA mode and the thermal conductivity properties of the fluid, i.e., the thermal conductivity and heat capacity. The heating current needed for the respective heating elements 50 and 60 when the velocity of flow of the fluid equals zero is used for calibrating the zero point of the characteristic describing the relationship between the velocity of flow and the heat transfer for the usual CTA operation and characterizes the quiescent point of the CTA bridge circuit.

Figure 3:
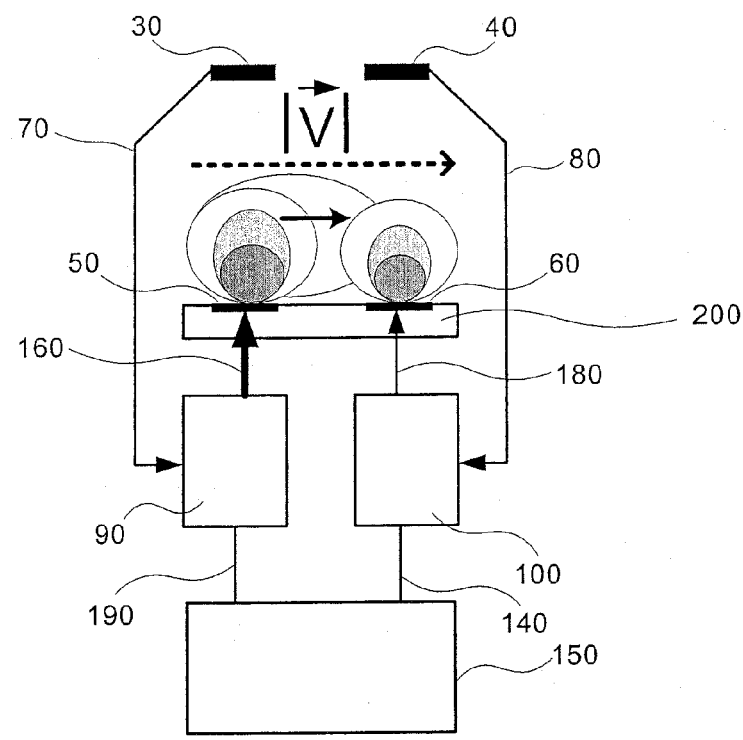
FIG. 3 is a schematic view showing the behavior of a sensor chip, as it is known from the state of the art, during a fluid flow.

FIG. 3 schematically shows the behavior of the sensor chip 200 from FIG. 2 during fluid flow from left to right. The flow vector $\overline{v}$ of the fluid is indicated in FIG. 3 by an arrow pointing from left to right, which is drawn in broken line, so that heating element 50 is located upstream and heating element 60 downstream. The temperature level lines no longer have a symmetrical distribution due to the convection of the fluid flow, but a heat transfer is obtained, which follows the fluid flow and is indicated by the arrow drawn in solid line. Due to the cooling fluid flow, the heating currents needed in the two heating elements 50 and 60 will be greater than the heating current needed when the velocity of flow of the fluid equals zero. However, the heating currents are no longer equal, because when the fluid heated by heating element 50 reaches heating element 60, it does not need to be heated so strongly any more to maintain a constant overtemperature, as this is the case within heating element 50. An analysis unit 150, which is connected to both bridges 90 and 100 via the electrical conductors 190 and 140, can utilize the difference of the heating currents to determine the direction of flow. In addition, it is known that the particular heating currents and/or the difference can be used to determine the velocity of flow of the fluid in the CTA mode.

Figure 4:
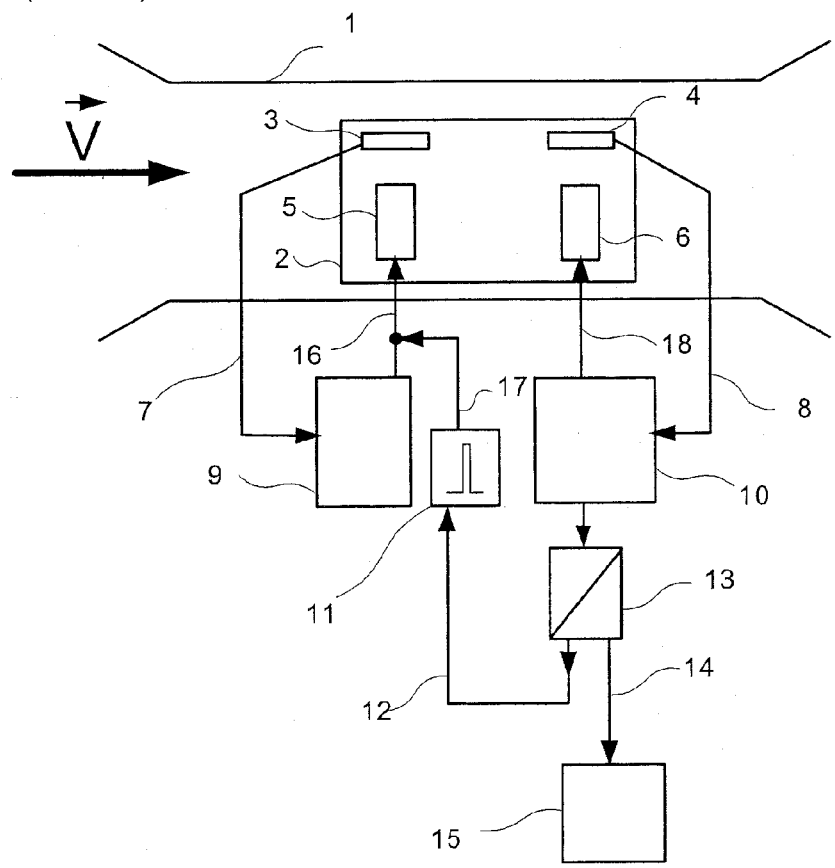
FIG. 4 is a schematic view showing the general layout of an advantageous embodiment of the device according to the present invention.

FIG. 4 shows a schematic layout of an advantageous embodiment of the device according to the present invention. Two thermal sensor elements 5 and 6 are arranged at spaced locations from one another in the path of flow of the fluid along the longitudinal axis of the flow channel 1 in a flow channel 1, for example, a cell for use in respirators, on a membrane 2 at the inner wall of the flow channel 1. One each of the two sensor elements 5 and 6 is connected to the constant-temperature anemometer bridge circuits (CTA circuits) 9 and 10, respectively, via the respective electrical conductors 16 and 18. In addition, two fluid temperature measuring elements 3 and 4, one each of which is connected to the respective CTA circuits 9 and 10 via the respective electrical conductors 7 and 8, are arranged on membrane 2. The CTA circuits 9 and 10 are able to adjust the sensor elements 5 and 6 in the CTA mode to a selected overtemperature above the fluid temperature measured in the fluid temperature measuring elements 3 and 4. The flow vector $\overline{v}$ of the fluid is indicated in FIG. 4 by an arrow, which is drawn in solid line and points from left to right, so that the fluid flows through the flow channel 1 from left to right in this example and the sensor element 5 is located upstream and the sensor element 6 downstream. A heating pulse generator 11 is connected via the electric conductor 17 to the electric conductor 16 and thus to the sensor element 5. A voltage pulse generated in the heating pulse generator 11 leads to a corresponding current pulse in sensor element 5, which leads to a corresponding evolution of heat in the sensor element 5 and in turn to an increase in the resistance in the sensor element 5 (not shown). The electric power transformed at the resistor is released in the form of thermal energy to the fluid surrounding the sensor element 5 in the form of a thermal signal. The thermal signal consequently consists in this example of a short-term heating of the fluid surrounding the sensor element 5, which heating goes beyond the conventional regulation to a certain overtemperature in the CTA mode. The thermal signal is carried by convection with the fluid flow to the sensor element 6 located downstream. When the thermal signal reaches the sensor element 6, less heating current is needed for the sensor element 6 for the duration of the signal than before or afterwards, since the CTA circuit 10 does not need the energy transmitted by the thermal signal to the sensor element 6 for heating to the overtemperature. The thermal signal received by the sensor element 6 is thus converted by the CTA circuit into an electric signal. A conversion unit 13 receives this electric signal and returns it via a feedback 12 and the heating pulse generator 11 to the sensor element 5. The returned electrical signal is transmitted by the heating pulse generator 11 in the form of a voltage pulse, which leads to the generation of a new thermal signal in the sensor element 5. Thus, this feedback leads to a certain signal frequency of feedback pulse signals. On the whole, a proportional relationship is to be expected between the velocity of flow and the signal frequency in this so-called pulsed operation, and, in particular, it is to be expected that a constant frequency of feed pulse signals will be obtained at constant velocity of flow between the sensor elements 5 and 6. The signal frequency is read in the conversion unit 13, for example, within the framework of an averaging, and the result is transmitted to the analysis unit 15 via the electrical conductor 14. The signal frequency is analyzed in the analysis unit 15 as an indicator of the velocity of flow of the fluid. External or other additional information, especially information that was obtained from a temporary CTA operation, may now be used as well.

Figure 5:
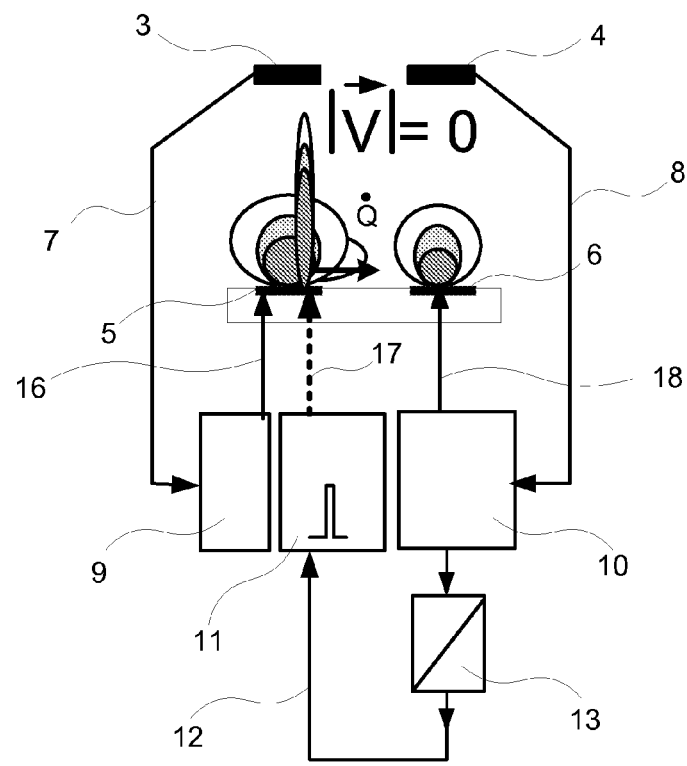
FIG. 5 is a schematic view showing the behavior of an advantageous embodiment of the device according to the present invention at zero velocity of flow.

FIG. 5 schematically shows the behavior of an advantageous embodiment of the device according to the present invention at zero velocity of flow. At zero velocity of flow, a thermal signal generated by the sensor element 5 does not reach the sensor element 6 at all, or at least it does not reach it in a certain minimum time, which corresponds to the distance between the sensor elements 5 and 6 divided by the minimum velocity of flow that can be measured in the pulsed operation. Consequently, no thermal signal is received by the sensor element 6, and a signal frequency equaling zero will be read.

Figure 6:
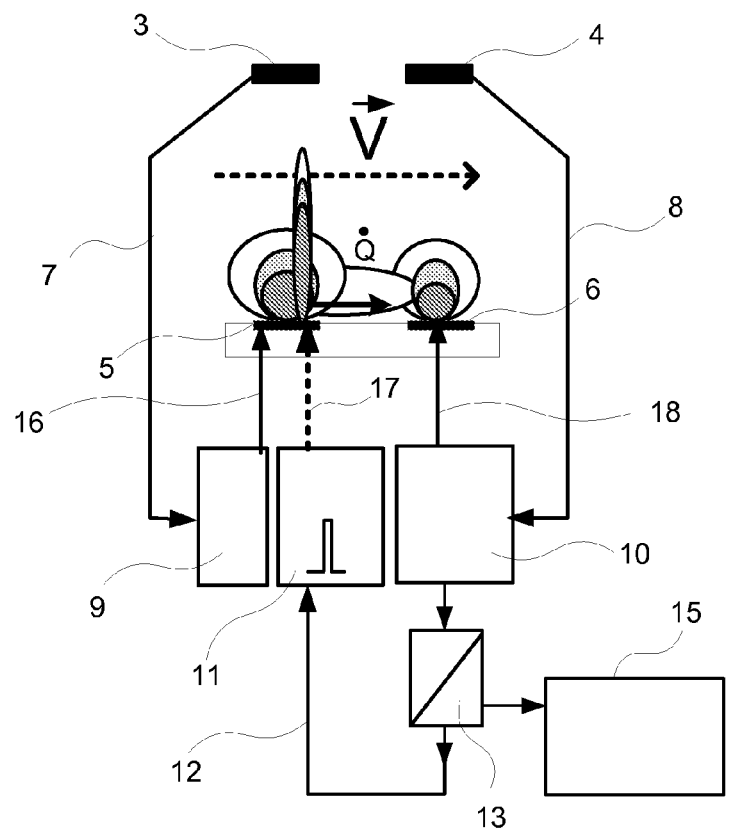
FIG. 6 is a schematic view showing the behavior of an advantageous embodiment of the device according to the present invention during a fluid flow.

FIG. 6 schematically shows the behavior of an advantageous embodiment of the device according to the present invention in case of a fluid flow from left to right. Analogously to FIG. 3, it is possible to operate the heating circuits of the sensor elements 5 and 6 in the CTA mode. In the embodiment being shown, the heating pulse generator 11 sends a feed pulse signal in the form of a voltage pulse to the sensor element 5 located upstream, which will thereupon generate a thermal signal and release it to the fluid as soon as the heating pulse generator 11 receives a feedback pulse signal from the conversion unit 13 via the feedback 12. The feedback pulse signal originates from the reception of a thermal signal in the sensor element 6 located downstream and continues to the conversion unit 13 in the form of a feedback pulse signal as a consequence of the heating capacity, which is needed less during the uptake of heat by the signal, measurable in the form of the heating current in the CTA circuit 10. The conversion unit 13 will then transmit the feedback pulse signal to the heating pulse generator 11 via the feedback 12. The conversion unit 13 is able to read the signal frequency of the feedback pulse signals, for example, by averaging over a certain period of time or number of signals. The signal frequency read is then made available via an electric conductor 14 to the analysis unit 15, which will then be able to determine the velocity of flow of the fluid from the signal frequency. The signal frequency can also be used together with other information in the analysis unit 15 so as to guarantee as error-free a determination of the velocity of flow as possible.

Figure 7:
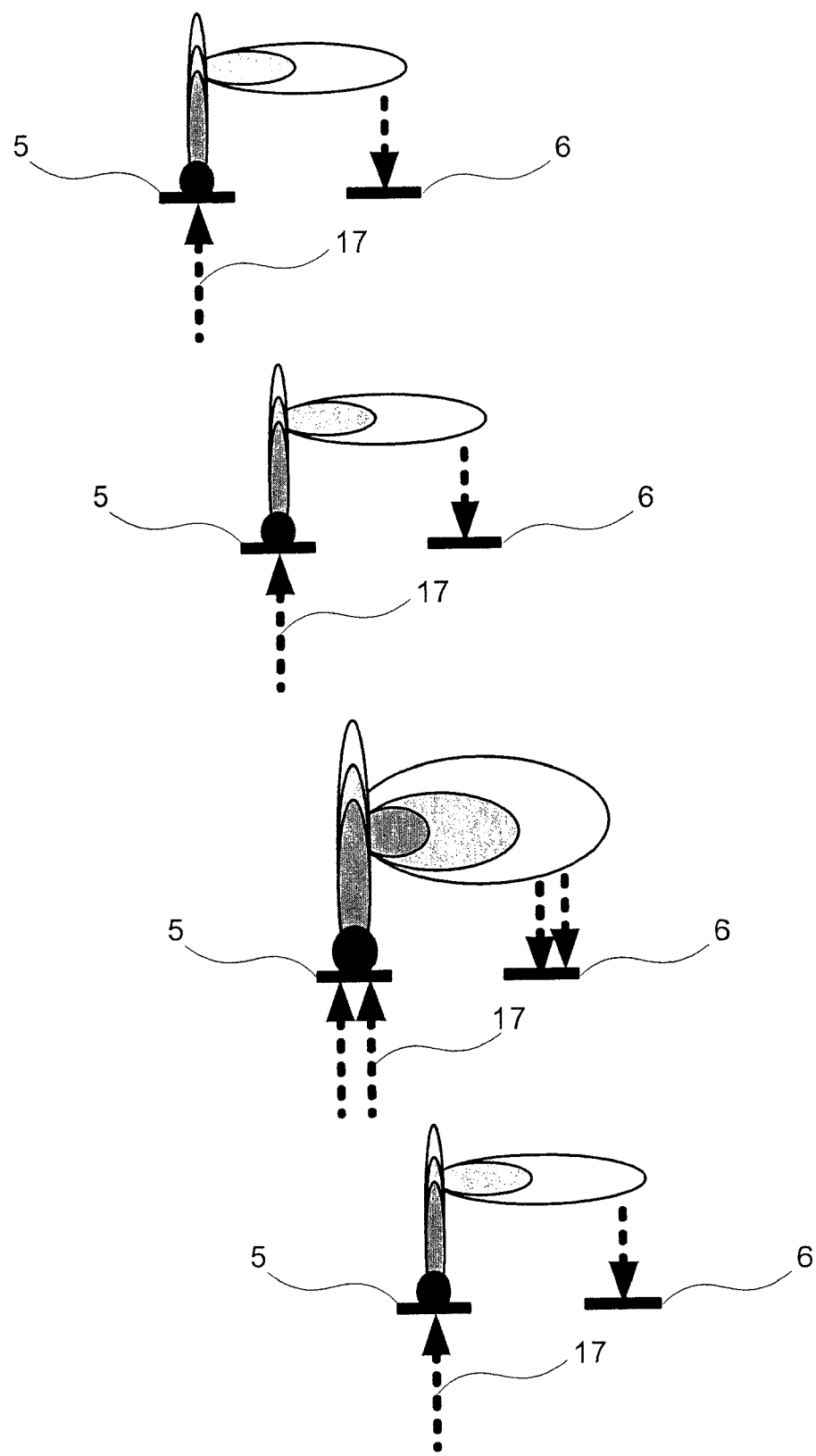
FIG. 7 is a schematic view showing the behavior of an advantageous embodiment of the device according to the present invention while the pulse amplitude is being varied in case of a gas x.
Figure 8:
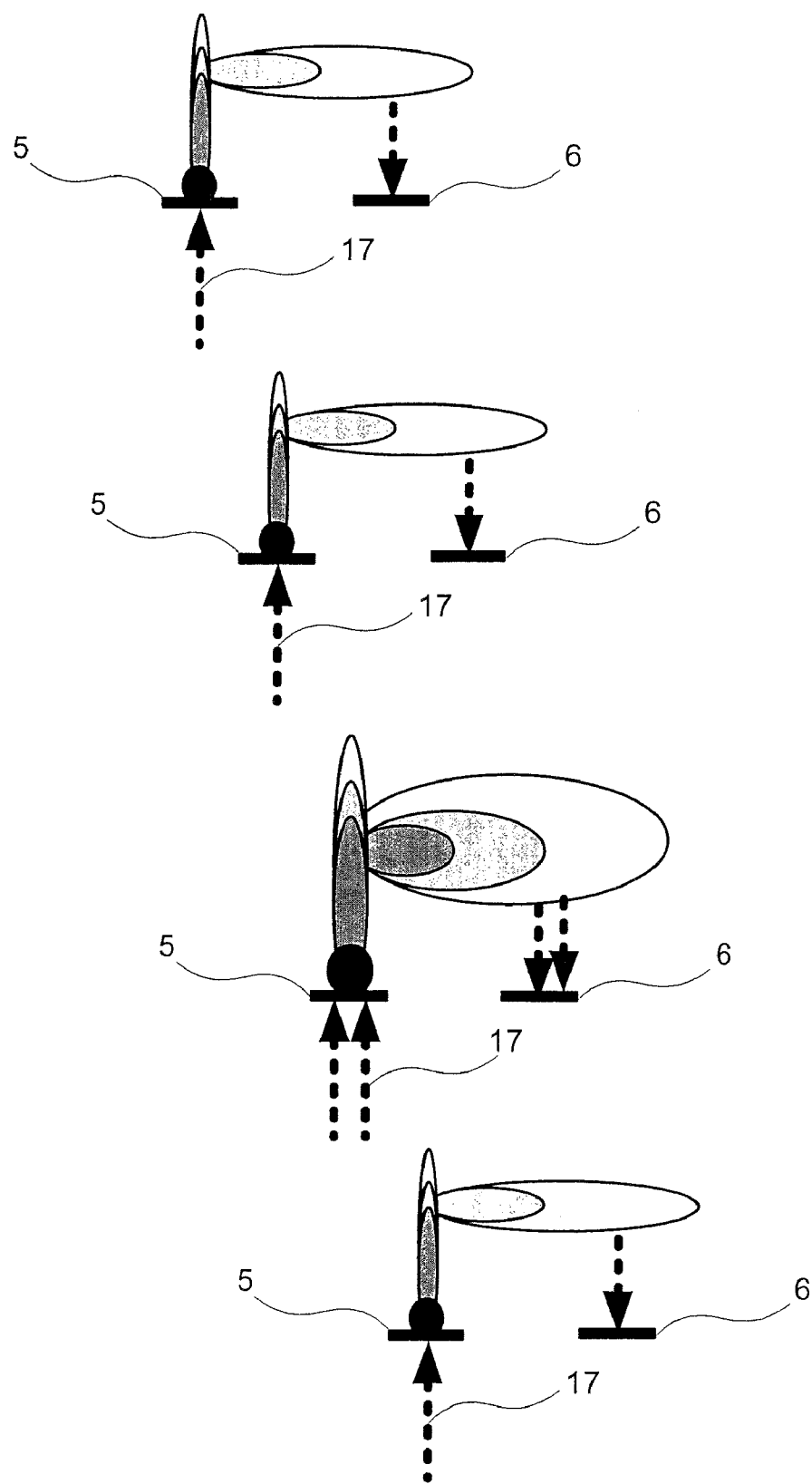
FIG. 8 is a schematic view showing the behavior of an advantageous embodiment of the device according to the present invention while the pulse amplitude is being varied in case of a gas y.

FIGS. 7 and 8 show a heating capacity modulation of the thermal signals in the form of voltage pulses. The gas used is a gas x in FIG. 7 and a gas y in FIG. 8. The third of four pulses each has twice as high an amplitude in both cases. This can be achieved by the heating pulse generator 11 being set such that two voltage pulses are transmitted within the pulse width to the sensor element 5 at every fourth feedback pulse signal detected. As an alternative, it would also be possible to modulate the length or amplitude of the voltage pulses when the pulse length is short enough compared to the pulse pauses. Not only the frequency of the feedback pulse signals, but also the information on the quantitative heat transfer from the sensor element 5 to the sensor element 6, which heat transfer is linked with the thermal signals, can be used with a modulated amplitude of the thermal signals. For example, the ratio of the heat transfer of every third of four thermal signals and the heat transfer taking place during the other three thermal signals in gas x (see FIG. 7) depends on the thermal conductivity properties of gas x. If, for example, the composition of gas x changes during the measurement, so that gas y possessing different thermal conductivity properties, such as thermal conductivity or heat capacity, prevails in the flow conduit, a different ratio of the heat transfer of every third of four thermal signals to the heat transfer taking place during the other three thermal signals may be obtained in gas y than in gas x (see FIG. 8). For the determination of the velocity of flow in the CTA mode, the change in the fluid from gas x to gas y would cause a misinterpretation as a change in the velocity of flow. The modulated pulsed operation can thus provide information on the change of the gas species, which can be used, corresponding to the particular prevailing gas composition, for the correct selection of the particular characteristic describing the relation between the velocity of flow and the heat transfer in a temporary CTA operation.

Figure 9:
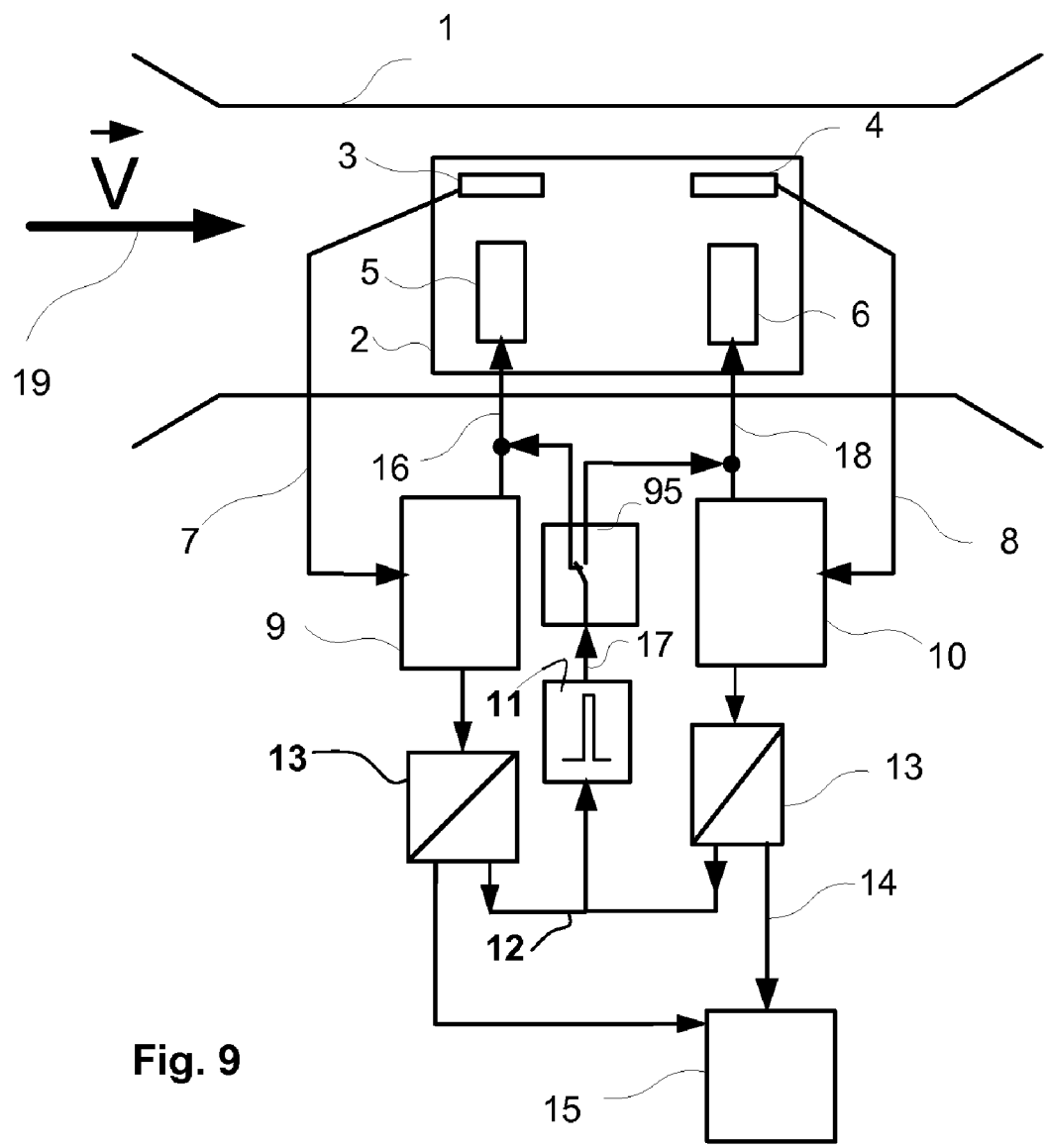
FIG. 9 is a schematic view that is similar to FIG. 4 showing the general layout of an advantageous embodiment of the device with a switchover unit according to the present invention.

FIG. 9 is a schematic view almost identical to FIG. 4 but also showing a switchover unit 95. The switchover unit 95 switches over the device such that a thermal signal received by the first sensor element 5 is returned to the second sensor element 6 in the form of a feedback pulse signal for a certain time in order to trigger the generation of a new thermal signal by the second sensor element 6. The signal frequency of the feedback pulse signals can thus be read and analyzed as an indicator of the velocity of flow of the fluid in the direction from the second to the first sensor element. The sensor elements 5 and 6 and the circuits connected thereto are advantageously of an identical design, so that a symmetrical arrangement is obtained, in which the switchover unit 95 can change the roles played by the sensor elements 5 and 6 as transmitters of thermal signals and as receivers of thermal signals between the two sensor elements 5 and 6. The switchover unit 95 preferably switches over the device periodically when the actual velocity of flow drops below a lower limit of the velocity of flow until a velocity of flow above this lower limit in one direction or the other can be detected. Consequently, there is here a certain range around a velocity of flow of zero, in which no information can be obtained on the velocity of flow.

Figure 10:
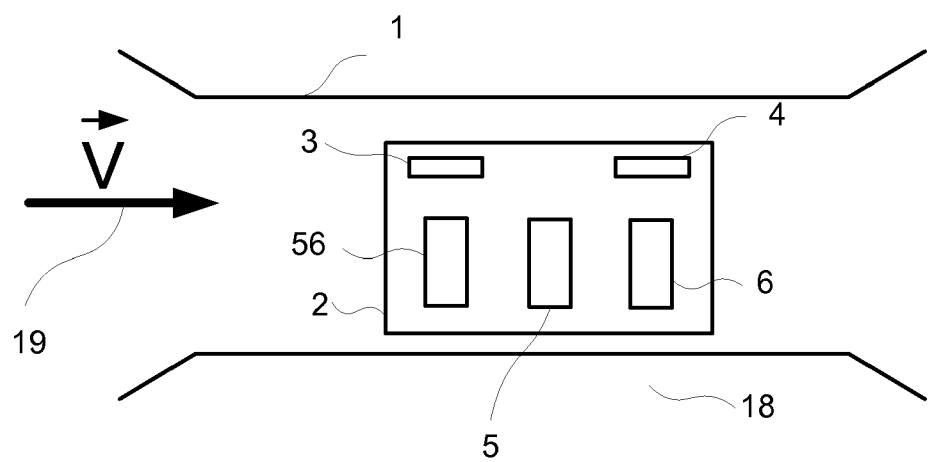
FIG. 10 is a schematic view that is similar to FIG. 4 showing a sensor chip in the flow channel with an additional third sensor element.

This drawback can be overcome in an alternative embodiment to the embodiment described above with reference to FIG. 9. FIG. 10 shows an alternative embodiment with a third sensor element 56, which is designed to detect a thermal signal from the fluid. The third sensor element 56 is arranged such that the first sensor element 5 is located at the flow path of the fluid between the second sensor element 6 and the third sensor element 56. The third sensor element 56 is connected to the first sensor element 5 via a second feedback, so that a thermal signal detected by the third sensor element 56 is returned in the form of a feed pulse signal to the first sensor element 5 in order to trigger the generation of a new thermal signal by the first sensor element 5. Analogously to the preceding exemplary embodiments, the controlling and analyzing means 15 is also connected to the second feedback and is designed to read and analyze the signal frequency of the feedback pulse signals in the two feedbacks as an indicator of the velocity of flow of the fluid in the direction from the first sensor element 5 to the third sensor element 56. Consequently, the velocity of flow is measured here basically in parallel in both directions of flow, so that the difference of the two measured velocities of flow is available with a sign corresponding to the direction of flow. Since a thermal signal moves in this case almost exclusively by convection in the direction of the fluid flow, that measured value "against the flow" yields a signal frequency of zero and thus also zero velocity of flow in the direction opposite the flow. Consequently, the simultaneous measurement in both directions does not distort the velocity of flow with a sign, which was determined by the difference.

While specific embodiments of the invention have been shown and described in detail to illustrate the application of the principles of the invention, it will be understood that the invention may be embodied otherwise without departing from such principles.

What is claimed is:

1. A device for measuring the velocity of flow of a fluid in a respiration system having a fluid flow path, the device comprising:

a first thermal sensor element;

a controllable heating element associated with said first thermal sensor;

a second thermal sensor element, said first thermal sensor element and said second thermal sensor element being arranged at spaced locations from one another at the fluid flow path of the respiration system, said first thermal sensor heating element generating a thermal signal, of a given duration, that is transmitted by the fluid flow along the fluid flow path from the first thermal sensor element to said second thermal sensor element and said second thermal sensor element detecting said thermal signal, of a given duration, from said fluid flow, and said second thermal sensor element being connected to said first thermal sensor element via a feedback connection such that each thermal signal, of a given duration, generated by said first thermal sensor element and detected by said second thermal sensor element brings about a return of a feedback pulse signal to said first thermal sensor element to cause said heating element of said first thermal sensor element to generate another thermal signal, of a given duration; and a controlling and analyzing means connected to said first thermal sensor element and said second thermal sensor element to start said generation of a first thermal signal, of a given duration, by said first thermal sensor element with a first pulse signal of a given duration determining a duration of the thermal signal and to read and analyze a signal frequency of said feedback pulse signals to determine the velocity of flow of the fluid during a further operation.

2. A device in accordance with claim 1, wherein at least one of said first thermal sensor element and said second thermal sensor element is a hot-film anemometer.

3. A device in accordance with claim 1, wherein at least one of said first thermal sensor element and said second thermal sensor element is connected to a constant-temperature anemometer circuit and can be analyzed in a constant-temperature anemometer mode.

4. A device in accordance with claim 1, further comprising a fluid temperature measuring element arranged and designed to measure said fluid temperature in an environment of one of said first thermal sensor element and said second thermal sensor element.

5. A device in accordance with claim 4, wherein at least one of said first thermal sensor element and said second thermal sensor element is connected to a constant-temperature anemometer circuit and can be analyzed in a constant-temperature anemometer mode and wherein said fluid temperature measuring element is connected to said constant-temperature anemometer circuit so that an amplitude of said thermal signals can be regulated as a function of said fluid temperature.

6. A device in accordance with claim 1, wherein said feedback connection comprises a heating pulse generator connected between said second thermal sensor element and said first thermal sensor element for transmitting said feedback pulse signal in a form of an electric heating pulse to said first thermal sensor element.

7. A device in accordance with claim 1, wherein said controlling and analyzing means comprises a conversion unit and a feedback and an analysis unit connected to said conversion unit.

8. A device in accordance with claim 1, further comprising a switchover unit wherein said second thermal sensor element has a controllable heating element associated therewith, said controllable heating element of said second thermal sensor element sending a thermal signal to said fluid, and said first thermal sensor element detecting a thermal signal generated by said second thermal sensor element from said fluid, said switchover unit switching over alternatingly, so that each thermal signal generated by said second thermal sensor element and detected by said first thermal sensor element brings about a return of a feedback pulse signal to said second thermal sensor element in order to trigger generation of another thermal signal by said heating element of said second thermal sensor element, and said controlling and analyzing means triggers said generation of a first thermal signal by said second thermal sensor element with a first pulse signal and reads and analyzes a signal frequency of said feedback pulse signal to determine the velocity of flow of the fluid in a direction from said second thermal sensor element to said first thermal sensor element.

9. A device in accordance with claim 1, further comprising a third thermal sensor element for detecting a thermal signal from said fluid, wherein said third thermal sensor element is arranged such that said first thermal sensor element is located at said fluid flow path of flow of said fluid between said second thermal sensor element and said third sensor element and is connected to said first thermal sensor element via a second feedback connection such that each thermal signal generated by said first sensor element and detected by said third thermal sensor element is returned in a form of a feedback pulse signal to said first thermal sensor element in order to trigger a generation of a new thermal signal by said first thermal sensor element, and said controlling and analyzing means is connected to said second feedback connection for reading and analyzing signal frequency of said feedback pulse signals to determine the velocity of flow of said fluid in said direction from said first sensor thermal element to said third thermal sensor element.

10. A device in accordance with claim 1, wherein an amplitude of said thermal signals can be modulated.

11. A device in accordance with claim 1, wherein said controlling and analyzing means determines heat transfer between said thermal sensor elements and to adjust said heating of one or more thermal sensor elements in response to changes in thermal conductivity properties of said fluid, which correspond to changes in heat transfer.

12. A process for measuring velocity of flow of a fluid in a respiration system with a flow path, the process comprising the steps of:
providing a first thermal sensor element with a controllable heating element in the flow path;
providing a second thermal sensor element in the flow path;
arranging said first thermal sensor element and said second thermal sensor element at spaced locations from one another in the fluid flow path of the respiration system so that a thermal signal generated by said first sensor element is transmitted by a flow of the fluid from said first thermal sensor element to said second thermal sensor element;
providing a first pulse signal triggered by a controlling and analyzing means;
generating a first thermal signal, of a given duration corresponding to a duration of the pulse signal, by said first thermal sensor element upon receiving said first pulse signal from said controlling and analyzing means;
detecting, with said second thermal sensor element, said first thermal signal generated by said first thermal sensor element and transmitted by the flow of the fluid;
generating a feedback pulse signal upon detecting said first thermal signal with said second thermal sensor element and sending said feedback pulse signal to said first thermal sensor element;
receiving the feedback pulse signal at said first thermal sensor element for triggering the generation of another thermal signal, of a given duration corresponding to a duration of the feedback pulse signal, by said first thermal sensor element and detecting subsequent thermal signals generated by said first thermal sensor element with each thermal signal generated by said first thermal sensor element and detected by said second thermal sensor element bringing about a sending of the feedback pulse signal during further operation; and
reading a signal frequency of said feedback pulse signals and analyzing the frequency to provide a read and analyzed signal frequency to determine the velocity of flow of the fluid during the further operation.

13. A process in accordance with claim 12, wherein at least one of said first thermal sensor element and said second thermal sensor element is analyzed in a constant-temperature anemometer mode during measurement for a certain time.

14. A process in accordance with claim 13, wherein during a time between thermal signals at least one of said first thermal sensor element and said second thermal sensor element is analyzed in said constant-temperature anemometer mode.

15. A process in accordance with claim 13, wherein at least one of said first thermal sensor element and said second thermal sensor element is analyzed in said constant-temperature anemometer mode at velocities of flow above a certain threshold.

16. A process in accordance with claim 13, wherein said read and analyzed signal frequency is used to select a suitable characteristic for said analysis in said constant-temperature anemometer mode.

17. A process in accordance with claim 13, wherein determined thermal conductivity properties of said fluid are used to select a suitable characteristic for said analysis in said constant-temperature anemometer mode.

18. A process in accordance with claim 13, wherein changes in determined thermal conductivity properties of said fluid are used to adjust a heating of one or more thermal sensor elements in a suitable manner.

19. A process in accordance with claim 12, further comprising measuring fluid temperature.

20. A process in accordance with claim 19, wherein one of said first thermal sensor element and said second thermal sensor element is heated to a certain basic temperature above said measured fluid temperature.

21. A process in accordance with claim 19, wherein heating of one of said at least one of said first thermal sensor element and said second thermal sensor element is adjusted in case of changes in said fluid temperature by taking into account said change in thermal conductivity properties of said fluid, which is associated with said change in temperature.

22. A process in accordance with claim 19, wherein an amplitude of said thermal signals is changed as a function of said measured fluid temperature.

23. A process in accordance with claim 19, wherein thermal conductivity properties of said fluid are determined by modulating an amplitude of said thermal signals and reading heat transfer between said thermal sensor elements.

24. A process in accordance with claim 12, wherein a direction of flow is recognized by a mode of operation of said thermal sensor elements being mutually switched over, so that said first sensor element detects a first thermal signal from said fluid, which said first thermal signal is generated by said second thermal sensor element, and each thermal signal detected by said first thermal sensor element is returned in a form of a feedback pulse signal to said second thermal sensor element in order to trigger generation of a new thermal signal by said second thermal sensor element, and said signal frequency of said feedback pulse signals is read and analyzed to determine the velocity of flow of said fluid in a direction from said second sensor thermal element to said first thermal sensor element.

25. A process in accordance with claim 12, wherein a direction of flow is recognized such that a first thermal signal from said fluid, which was generated by said first thermal sensor element, is detected by means of a third thermal sensor element, which is arranged such that said first thermal sensor element is located at said fluid flow path between said second thermal sensor element and said third thermal sensor element, and each thermal signal detected by said third sensor element is returned in a form of a feedback pulse signal to said first thermal sensor element in order to trigger said generation of a new thermal signal by said first thermal sensor element, and said signal frequency of said feedback pulse signals is read and analyzed to determine the velocity of flow of said fluid in said direction from said first thermal sensor element to said third thermal sensor element.

* * * * *